(12) United States Patent
Raisch

(10) Patent No.: US 8,763,603 B2
(45) Date of Patent: Jul. 1, 2014

(54) METHODS AND DEVICES FOR RESCUING A DISTRESSED DIVER

(76) Inventor: Netanel Raisch, Psagot (IL)

( * ) Notice: Subject to any disclaimer, the term of this patent is extended or adjusted under 35 U.S.C. 154(b) by 480 days.

(21) Appl. No.: 12/791,027

(22) Filed: Jun. 1, 2010

(65) Prior Publication Data

US 2011/0290247 A1 Dec. 1, 2011

(51) Int. Cl.
| | | |
|---|---|---|
| *B63C 11/02* | (2006.01) | |
| *A61B 5/087* | (2006.01) | |
| *B63C 11/22* | (2006.01) | |
| *A61B 5/08* | (2006.01) | |
| *A62B 27/00* | (2006.01) | |
| *G08B 3/00* | (2006.01) | |
| *G08B 5/00* | (2006.01) | |
| *A62B 7/00* | (2006.01) | |
| *A61M 15/00* | (2006.01) | |
| *A62B 9/00* | (2006.01) | |
| *A61M 16/00* | (2006.01) | |

(52) U.S. Cl.
CPC ......... *B63C 11/2245* (2013.01); *A61B 2503/10* (2013.01); *A61B 5/087* (2013.01); *A61B 5/0826* (2013.01)
USPC ............. 128/201.27; 128/202.22; 128/202.14

(58) Field of Classification Search
CPC ........ B63C 11/02; B63C 11/24; B63C 11/06; B63C 11/18; B63C 11/202; B63C 11/2245; B63C 11/22; B63C 9/1255; B63C 11/08; A61M 16/00; A61M 2016/0039; A61M 16/0051; A62B 9/006; A62B 18/088
USPC ............. 128/201.27, 200.24, 204.22, 204.26, 128/205.22, 202.22, 203.13, 202.14, 128/204.18, 204.21, 204.23; 2/102; 600/529; 405/186, 185, 187; 340/573.6; 114/334

See application file for complete search history.

(56) References Cited

U.S. PATENT DOCUMENTS

| | | | | | |
|---|---|---|---|---|---|
| 4,926,703 | A | * | 5/1990 | Budinger | 73/865.1 |
| 5,038,774 | A | * | 8/1991 | Chabert | 128/205.24 |
| 5,517,199 | A | * | 5/1996 | DiMattei | 342/357.31 |
| 5,912,615 | A | * | 6/1999 | Kretzmar et al. | 340/426.12 |
| 6,154,140 | A | * | 11/2000 | Thorpe et al. | 340/573.6 |
| 7,839,291 | B1 | * | 11/2010 | Richards | 340/573.6 |
| 8,033,755 | B2 | * | 10/2011 | Stood et al. | 405/186 |
| 2008/0266118 | A1 | * | 10/2008 | Pierson et al. | 340/573.6 |
| 2009/0217927 | A1 | * | 9/2009 | Stood et al. | 128/202.14 |

* cited by examiner

*Primary Examiner* — Jackie T Ho
*Assistant Examiner* — Mark Wardas

(57) ABSTRACT

The invention discloses devices and methods for identifying a diver in distress and initiating a rescue response. Specifically, embodiments of the present invention allow for identification of a diver who is not breathing properly and in response giving local stimuli to allow the diver to response. Should he/she not respond, the instant invention will initiate steps to bring the diver back to the water surface and alert others as to his/her need of assistance.

16 Claims, 14 Drawing Sheets providing a sensor for measuring air pressure in a diver's breathing system, wherein the sensor is in electric communication with an electronic controller;

measuring air pressure patterns of the diver over periods of time with the controller;

determining a change in the air pressure pattern is present wherein the change exceeds a predetermined value ; and,

activating a response element in response to the change in the air pressure pattern.

FIG. 9

METHODS AND DEVICES FOR RESCUING A DISTRESSED DIVER

FIELD AND BACKGROUND OF THE INVENTION

The present invention, in some embodiments thereof, relates to methods for automatically aiding a distressed diver and, more particularly, but not exclusively, to methods for rapidly bringing a diver to the surface.

Diving is an inherently dangerous activity. Divers typically go down meters into ocean or fresh water and rely solely on air tanks and breathing devices for continued oxygen consumption and carbon dioxide removal. Diving is a popular recreation sport and is a required activity in diverse fields such as warfare, shipping, and tourism.

A diver typically has an air tank with associated regulators and tubing for delivery of compressed air at an appropriate pressure to a mouth-based breathing device. As divers can be tens of meters under the water surface and are often out of communication with others for extended periods of time, risks of air tank failure are potentially fatal. Divers, like all humans, have a small window during which they can survive without oxygen or air being delivered to the lungs. A diver in distress suffers from his watery surroundings as well as his disconnection from other divers and/or those in a boat from which he was delivered to the water.

U.S. Pat. No. 4,176,418 to Scott describes an apparatus for automatic inflation of a diver flotation device in response to cessation of breathing by the diver, or in response to pressure reduction of the air source to a predetermined reserve pressure. The apparatus includes high and low pressure systems, the low pressure system being coupled to the diver flotation device and to the diver breathing device. A pair of valves interposed between the high and low pressure systems are responsive to termination of diver breathing and reduction of the source pressure to a predetermined reserve pressure, respectively, to open and allow air from the high pressure system to pass into the low pressure system. This inflates the flotation device and brings the diver to the surface U.S. Pat. No. 5,156,145 to Flood et al. teaches a self-contained breathing apparatus for use in a noxious or oxygen-deficient atmosphere with redundant first stage pressure reducers and redundant second stage demand regulators which together serve as an automatic by-pass control in the event of a failure in the closed position of a first stage pressure reducer or a second stage demand regulator. A helmet with a face mask and inflatable helmet adjusting device for sizing the helmet to the user's head, provided impact protection and applying pressure to the back of the head causing the face to come into contact with the face mask resulting in the air-tight enclosure of the user's face in the oral-nasal area of the helmet. An integral pump and valve mechanism located in the helmet and operated by pushing on a bulb with the thumb or forefinger compresses air into a bladder thereby sizing the helmet and forming the air-tight seal of the face mask to the user's face. A combination manually operated pump, suction valve and relief valve permit ambient air to be compressed into the helmet bladder without leakage while excess pressure is discharged by depressing the relief valve on the helmet exterior.

U.S. Pat. No. 5,516,233 to Courtney teaches a water safety and survival system that provides a multi-chambered personal flotation device that operates on minimal volume to create a single heads up righting moment that reliably stabilizes an unconscious victim with his airway out of the water. This is accomplished with a minimal amount of lift, less deflated bulk, improved cosmetic appeal and reduced cost. These combined advances result in a safety vest conducive to actually being worn, a key feature for a safety vest. The system also provides for incorporation of a separating second inflatable life ring, rescue board, artificial respiration assist platform and ultimately a raft for removal of the victim from the water to protect him from hypothermia. This sequentially inflated, multi-chambered, multifaceted inflatable rescue product is incorporated within the body of the safety vest. The incorporation of a wide range of rescue products into the body of the personal flotation device will reduce the incidence of that dual tragedy that occurs when the rescuer becomes the second victim. This water survival system when adapted to the special needs of the scuba diver requires the incorporation of a tank compensating keel to offset the deleterious effects of a buoyant empty tank whose buoyancy can force the diver's airway under the water. Further adaptation for use underwater also includes a system to adjust the volume of the primary buoyancy compensation chamber and variable valve for segregation and reliable regulation of one or more additional surface flotation chambers underwater. The design of the separating chambers coincides with responsibilities and goals of the diver. These and more modifications for the safe underwater use of the heads up safety vest are critical in order to mitigate the risk of rapid ascent and its consequences, arterial gas embolism and decompression sickness.

U.S. Pat. No. 4,645,465 also to Courtney describes scuba gear for use by divers and the like for carrying a compressed air tank to provide an underwater source of oxygen, a backpack being adapted for securing the tank to the diver and including quick release components for permitting the diver to rapidly free himself of the tank, an inflatable transport raft being secured to the tank and held in compact and gathered form by releasable fasteners in order to permit the raft to open in response to internal inflation pressure, the backpack being adapted for connection to the diver's upper torso together with a separate vest type buoyancy compensator, the backpack being adapted to permit inflation of the buoyancy compensator if desired and also permitting separation of the tank with the buoyancy compensator remaining in place on the diver, the transport raft providing flotation for the tank when the tank is freed from the diver, the raft also providing transport for the diver on the surface of the water.

U.S. Pat. No. 5,800,228 to Hernandez teaches a permanently wearable self-rescue system for free divers and others engaged in aquatic pursuits to recover to the surface of the water if they should become disabled for any reason. Prior to or during ascent from a dive, if the free-diver has any feeling of insecurity or danger or just wants to insure a totally safe ascent, he or she arms a trigger mechanism that is preferably held in the armed position by the diver's hand grip. If the free-diver should lose consciousness or otherwise be incapacitated, his or her hand grip is released and the trigger mechanism is actuated which results in a resiliently biased puncture pin being propelled to puncture a gas cartridge. Pressurized gas from the cartridge is then directed to an economically designed inflatable bladder garment. The bladder garment is especially designed so that it offers little hydrodynamic resistance when underwater and thus is compatible with the frequent dives taken by free-divers during a typical outing. Further, a locking pin is provided so that the puncture pin can be maintained in a locked or standby position when the free diver does not require or does not want activation of the self-rescue system such as would be the case during normal dives, surface intervals, temporary storage, etc. This locking pin can be either manually or automatically disengaged at any time by the user.

The prior art does include methods and devices for aiding a distressed diver. Most of the systems rely on mechanical means for aiding a diver who has either stopped breathing or is no longer receiving oxygen in a proper manner.

SUMMARY OF THE INVENTION

It is therefore a purpose of the present invention, in some embodiments, to describe methods and devices for rescuing a diver in distress, wherein changes in breathing behavior or gas pressure generate a response that brings a diver quickly to the water surface.

The invention provides a device for rescuing a diver in distress, including: an air pressure sensor for determining air pressure in the diver's breathing system; an electronic controller; a power source with an on/off switch; and, at least one response element.

In one aspect of the device, the sensor is placed in a high pressure environment In another aspect of the device, the sensor is placed in a medium pressure environment.

In another aspect of the device, the sensor is placed in a low pressure environment.

In another aspect of the device, the sensor and the electronic controller are realized as a single element.

In another aspect of the device, the power source is realized as rechargeable batteries.

In another aspect of the device, the at least one response element includes an inflatable vest.

In another aspect of the device, the at least one response element includes an inflatable balloon.

In another aspect of the device the at least one response element includes a belt having a plurality of weights.

The invention additionally includes a method for rescuing a distressed diver, including: providing a sensor for measuring air pressure in the diver's breathing system, wherein the sensor is in electric communication with an electronic controller; measuring air pressure patterns of the diver over periods of time with the controller; determining a change in the air pressure pattern is present wherein the change exceeds a predetermined value; and, activating a response element in response to the change in the air pressure pattern.

In one aspect of the method, there is an additional step of training the sensor as to the breathing patterns of the diver.

In another aspect of the method, there is an additional step of alerting an authority as to the distress state of the diver.

In another aspect of the method, the response element includes any of the following features: lights, sounds, voice, and vibration.

In another aspect of the method, the response element includes a buoyancy component.

In another aspect of the method, there is an additional step of modifying the diving depth of the diver.

In another aspect of the method, the periods of time are predetermined.

In another aspect of the method, the periods of time are determined by the controller.

The invention also provides a method for rescuing a distressed diver, including: providing a sensor for air measuring air pressure in said diver's breathing system, wherein the sensor is in electronic communication with an electronic controller device; determining that the diver is not breathing; activating an alarm; and, changing the buoyancy of the diver.

In one aspect of the method, the alarm may be turned off by the diver.

In another aspect of the method, the changing of the buoyancy is accomplished automatically through diverting some of the diver's air via a valve to the diver's inflator.

Unless otherwise defined, all technical and/or scientific terms used herein have the same meaning as commonly understood by one of ordinary skill in the art to which the invention pertains. One term, "diver rescue element" may mean a device, element, or unit that aids in bringing a diver to the water surface. A diver rescue element generally may include a gas pressure or breathing monitor as well as a control element. The control element can both monitor gas pressure or diver breathing, as well as invoke a plurality of appropriate responses to any anomalies recorded with respect to gas pressure or diver breathing. A diver rescue element may include additional elements such as transponders, GPS chips, WiFi elements, and more. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. It is noted that similar elements in various drawings will have the same number, advanced by the appropriate multiple of 100.

In the drawings:

FIG. 9 is a flowchart for a method associated with the present invention;

DESCRIPTION OF SPECIFIC EMBODIMENTS OF THE INVENTION

The present invention, in some embodiments thereof, relates to a diver rescue system and, more particularly, but not exclusively, to methods and devices for determining that a diver is not breathing or receiving air and then automatically taking appropriate action so as to either revive the diver and/or get him/her to the water surface for rescue.

Figure 1:
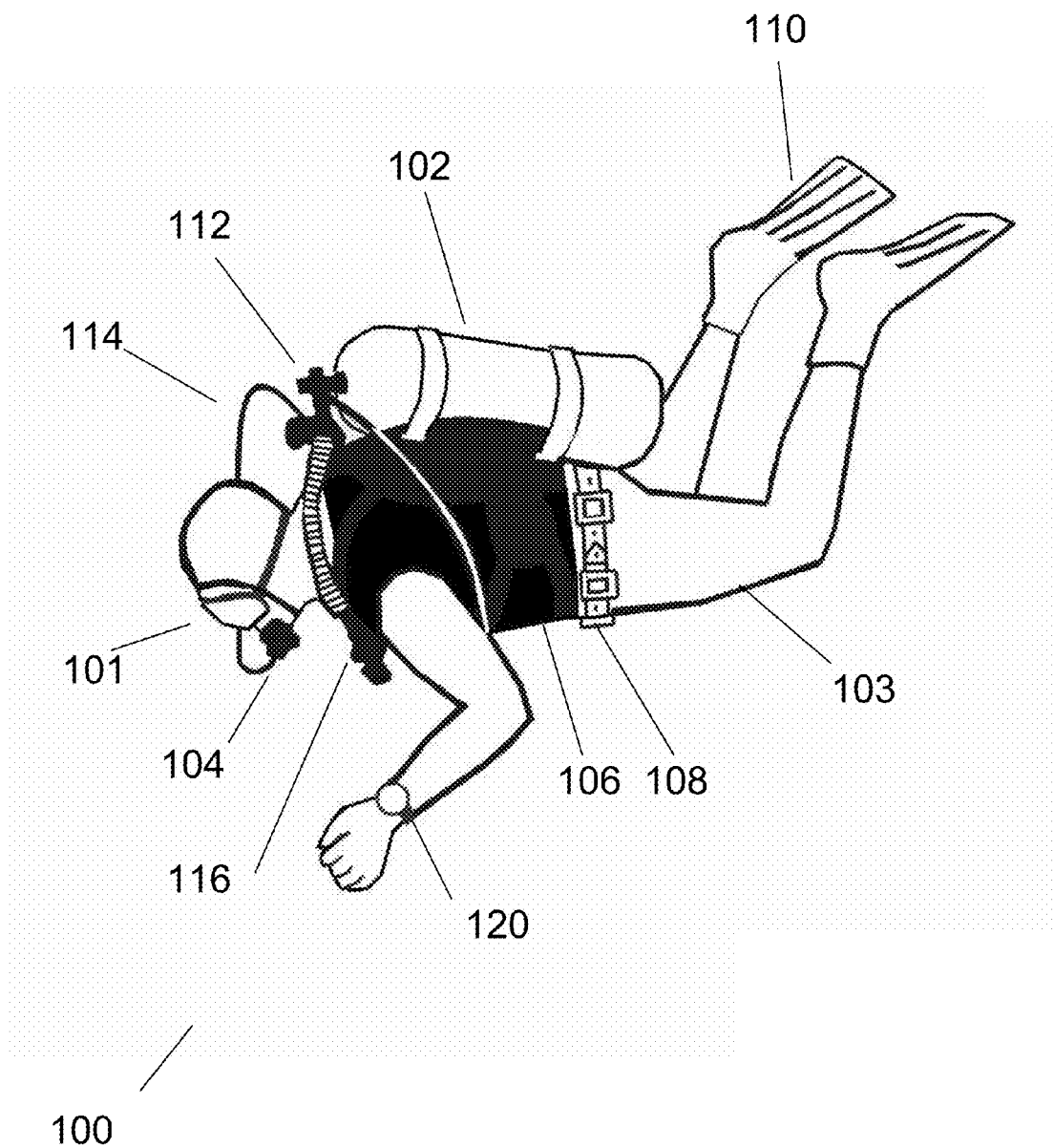
FIG. 1 is a schematic representation of diver in water.

For purposes of better understanding some embodiments of the present invention, as illustrated in FIGS. 1-11 of the drawings, reference is first made to the construction and operation of a localized drug release system as illustrated in FIG. 1.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 illustrates a diver 100 with a mask 101, tank 102, wetsuit 103, mouth piece 104, inflatable vest 106, ballast belt 108, and fins 110. The tank 102 includes a regulator 112 as well as a hose 114 that allow for passage of air or oxygen from tank 102 to the breathing unit 104. An inflator 116 is shown connecting the regulator 112 optionally to the inflatable vest 106. A watch 120 may provide depth and other pertinent data. It is understood that additional components and materials may be present on a diver 100 at the time that he/she dives, but those elements are not shown in this figure for ease of view of those components listed above. It is understood that the present invention has application to military, recreational, professional and other divers as well as fishermen.

First Embodiment

Figure 2:
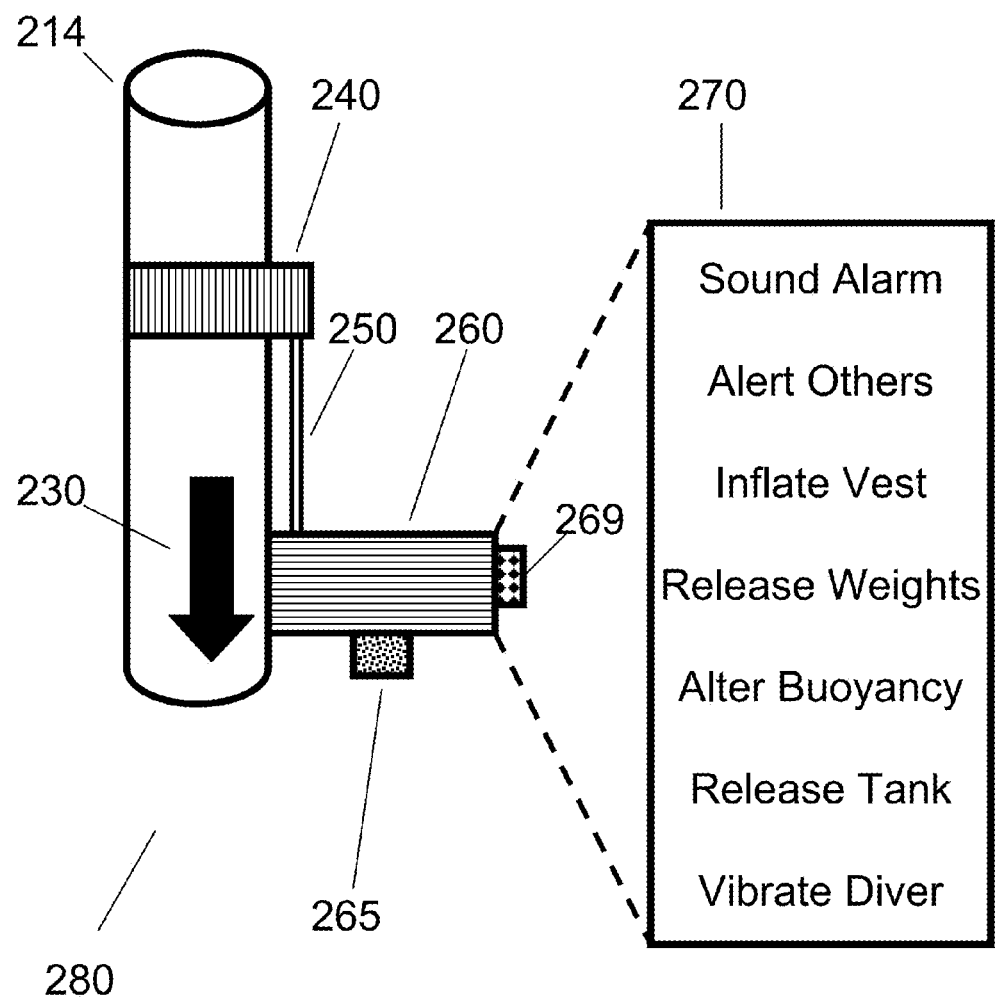
FIG. 2 is a schematic representation of components of the present invention.

Referring now to FIG. 2, a diving hose 214 allows for unidirectional flow 230 of oxygen or air from a tank (not shown) to a diver's mouth piece or to an inflator (not shown). A gas pressure sensor 240 measures the pressure associated with said flow 230 at all times during diving. The gas pressure sensor 240 is generally in contact with the flow 230 of gas either directly or indirectly. As shown, the gas pressure sensor 240 sits partially in the diving hose 214. Alternatively, some piping (not shown) can allow for gas to reach the gas pressure sensor 240 without the latter being in the direct flow 230 of gas to a diver. The gas pressure sensor 240 is in electrical connection 250 with a controller unit 260. The controller unit monitors gas pressure changes during a dive. The controller unit 260 is preprogrammed with gas pressure behavior either in general or for a particular diver. The controller unit 260 continually monitors data from the gas pressure sensor 240 and compares said data to preprogrammed gas pressure behavior. Should there be a cessation in the change of gas pressure (constant gas pressure recorded implying the diver is not breathing) or should the changes in gas pressure deviate by a predetermined amount from expected behavior over a predetermined period of time (suggesting erratic diver behavior), the controller unit 260 can invoke one or a plurality of responses 270 to help and/or save the diver. In typical prototype devices, 15 seconds represent the period of time during which a significant change in gas pressure behavior will elicit a response 270 although more or less sampling time may be utilized. Responses 270 shown in FIG. 2 are by no means limiting. A response 270 may include vibrating an element in contact with the body of the diver in order to wake him/her up. Alternatively, lights or sound might be activated to alert the diver of a change in gas pressure behavior. Should the diver be able to respond to these or similar stimuli, he/she can push an on/off button 265 on or associated with the controller unit 260 that would reset the controller unit 260 and end the response 270. Should 3-5 seconds of diver-specific responses (as described above) not lead to contact with the reset button 265, the controller unit 260 may take additional actions to allow for the diver's immediate return to surface. Such responses include inflation of a diving vest (not shown) or release of a ballast belt or a part thereof (not shown). The controller unit 260 can additionally alert others—fellow divers, ship-based crew or even land-based emergency units—that the diver is in danger. These latter responses 270 will be discussed in some of the embodiments described below. It is noted that the gas pressure sensor 240 and controller 260 work electronically and not mechanically. The diver rescue element 280 also includes an on/off switch 269 to turn on the system prior to diving and to turn it off after returning from diving.

Second Embodiment

Figure 3:
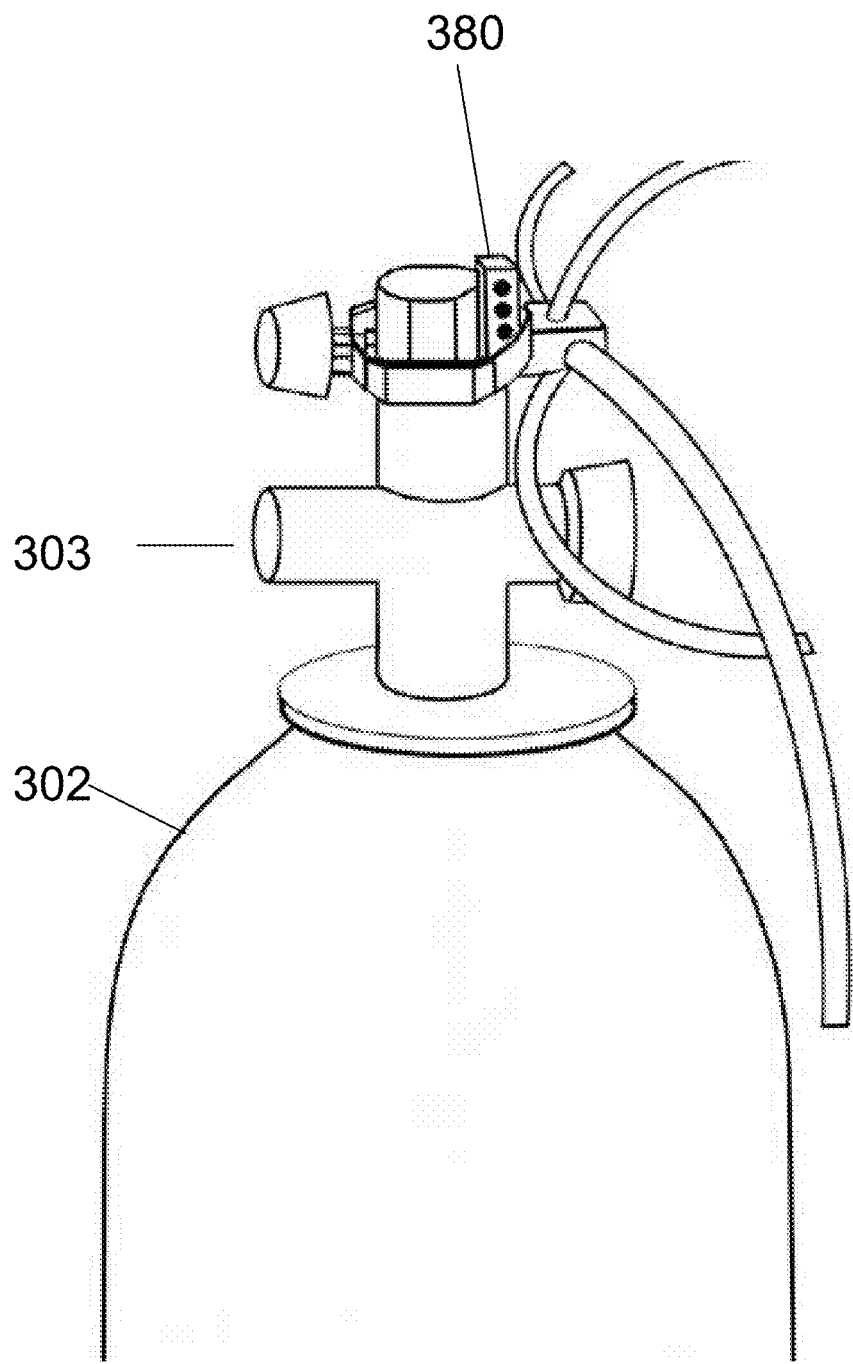
FIG. 3 is a schematic representation of an embodiment of the present invention.

Attention is turned to FIG. 3, wherein is shown diving gas tank 302 with a diver rescue element 380 that includes both a gas pressure monitor as well as a controller element (not shown separately in this example). The diver rescue element 380 is contacted to the high-pressure regulator 303 attached to the tank 302. Though the regulator measures the high pressure gas leaving the tank, the diver rescue element 380 may be placed in contact with high pressure gas flow and still function properly.

Third Embodiment

Figure 4:
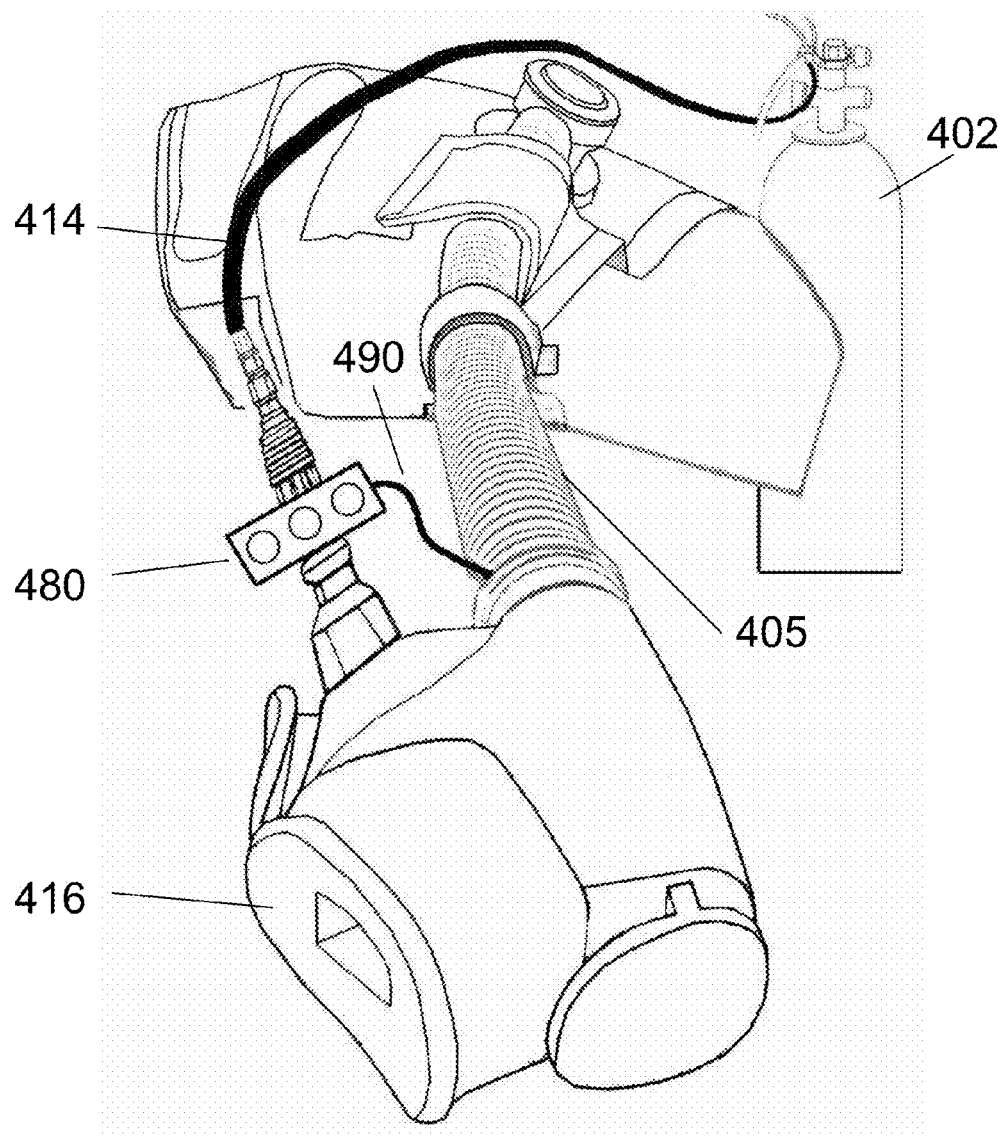
FIG. 4 is a schematic representation of an embodiment of the present invention.

Attention is turned to FIG. 4, which shows an alternative embodiment of the present invention. A diver rescue element 480 is placed along a hose 414 that has medium pressure gas coming from a tank 402 and is delivered to a diver's inflator 416. The diver rescue element 480 is connected 490 to the inflator hose 405 as shown. Should diver (not shown) stop breathing, as determined by anomalous breathing behavior, and should diver not respond to vibrations, sound or other local stimuli, the diver rescue element 480 can transfer air from the hose 414 to the inflator tube 404 in order to initiate ascent of the distressed diver.

A critical feature to note in the present invention is that all steps are performed automatically. The diver rescue element 480 monitors gas pressure from the tank to the driver without any required interference of the diver. Should there be a problem such as no breathing or inconsistent gas pressure, the diver rescue element 480 will first alert the diver through vibrations, lights, and/or sounds or the like. Should the diver not respond to the stimuli by pushing (within a few seconds) an on/off button (or reset button) associated with the diver rescue element 480, then the diver rescue element 480 will begin the process of automatically bringing the diver to the surface for air and proper assistance.

Fourth Embodiment

Figure 5:
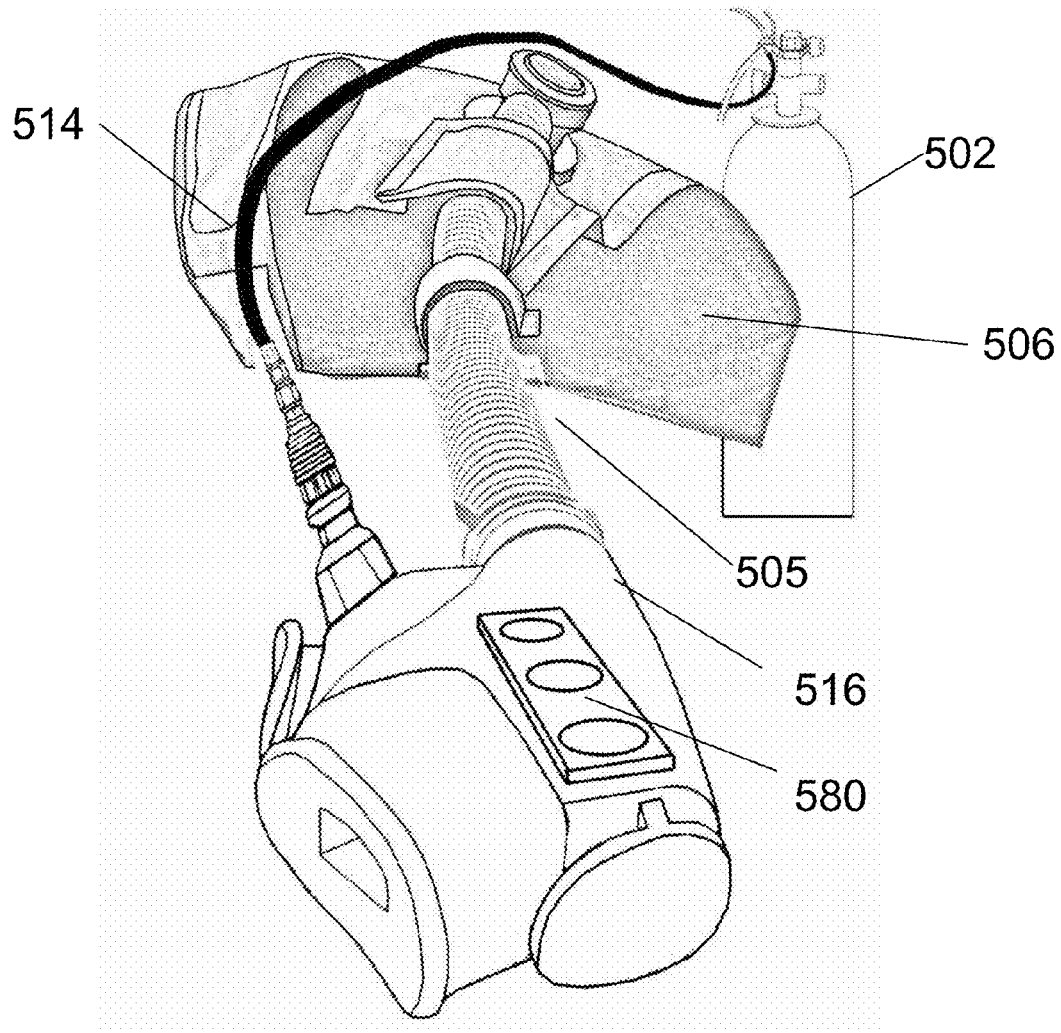
FIG. 5 is a schematic representation of an embodiment of the present invention.

Attention is now turned to FIG. 5 which shows an alternative embodiment of the invention. A diver rescue element 580 is associated directly with diver inflator 516 and measures changes in medium gas pressure. Should the diver be in distress and not respond to local stimuli initiated by the diver rescue element 580, then air from tank 502 will be delivered through tube 514 directly to the inflator hose 505, which can then begin to alter the buoyancy of the diver, so as to bring him/her to a less dangerous depth of water. For example, air from the tank 502 can be directed through the inflator 516 to an inflatable vest 506 or other element. Inflation of the vest 506 leads to diver climbing through the water towards the surface. Should the diver regain consciousness, he/she could reset the diver rescue element 580 and then manually use the inflator 516 to continue to rise or alternatively deflate the vest 506 in order to again descend the depths.

Fifth Embodiment

Figure 6:
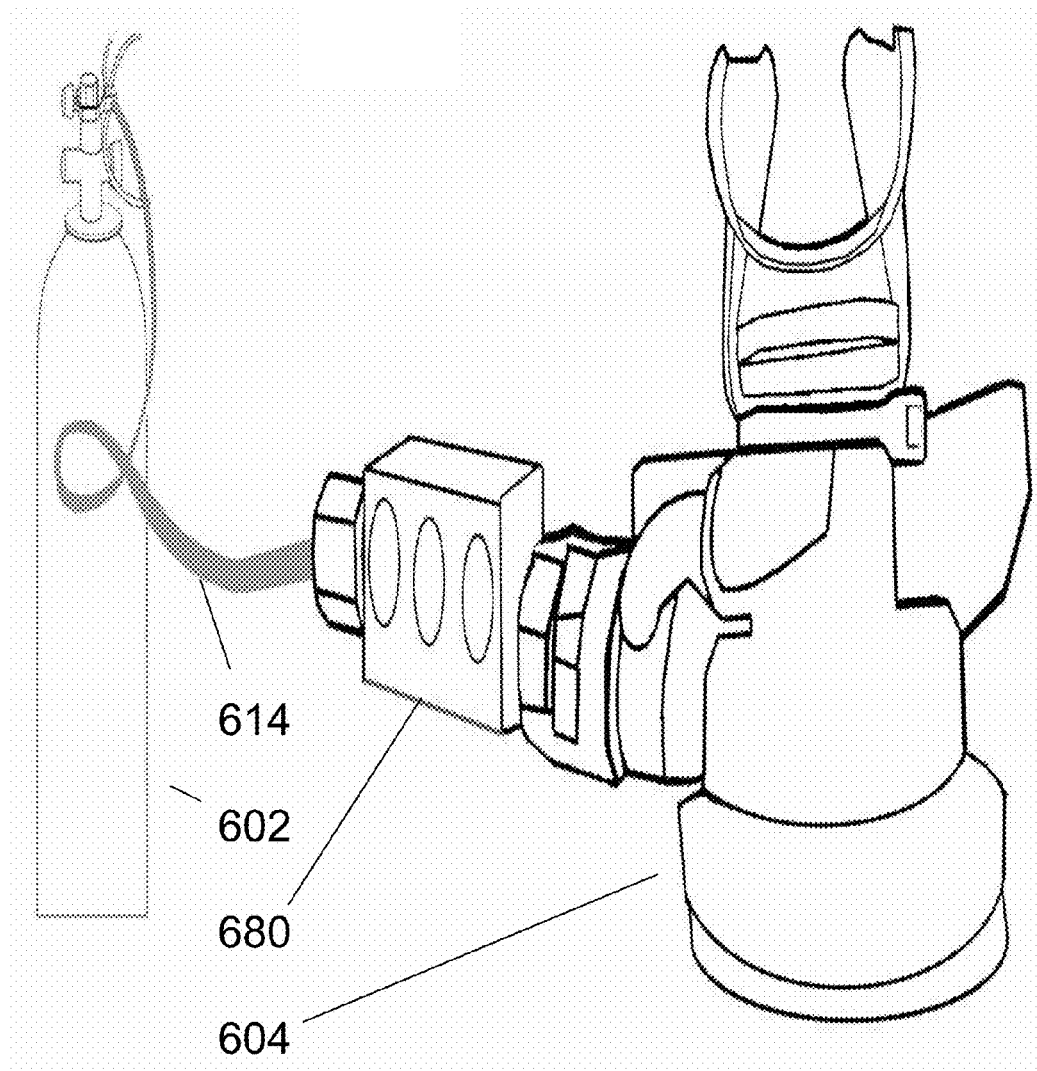
FIG. 6 is a schematic representation of an embodiment of the present invention.

Attention is now turned to FIG. 6 which shows an alternative embodiment of the present invention. A diver rescue element 680 is associated directly with the mouth piece 604 worn by a diver (not shown) and thus measures the low pressure gas that is delivered from tank 602 via a tube 614. This embodiment is the subject of the prototype example described below. As in all other embodiments, the diver rescue element 680 is preprogrammed to monitor expected gas pressure changes during normal breathing of a diver. In this embodiment, the diver rescue element 680 which includes both a gas pressure sensor and a control unit (not shown separately) measures gas pressure as a direct function of diver breathing. Should the gas pressure remain constant for a predetermined period of time (generally 15 seconds) or should their be anomalies in the pressure values, the diver rescue element 680 will initiate diver assistance.

Figure 7A:
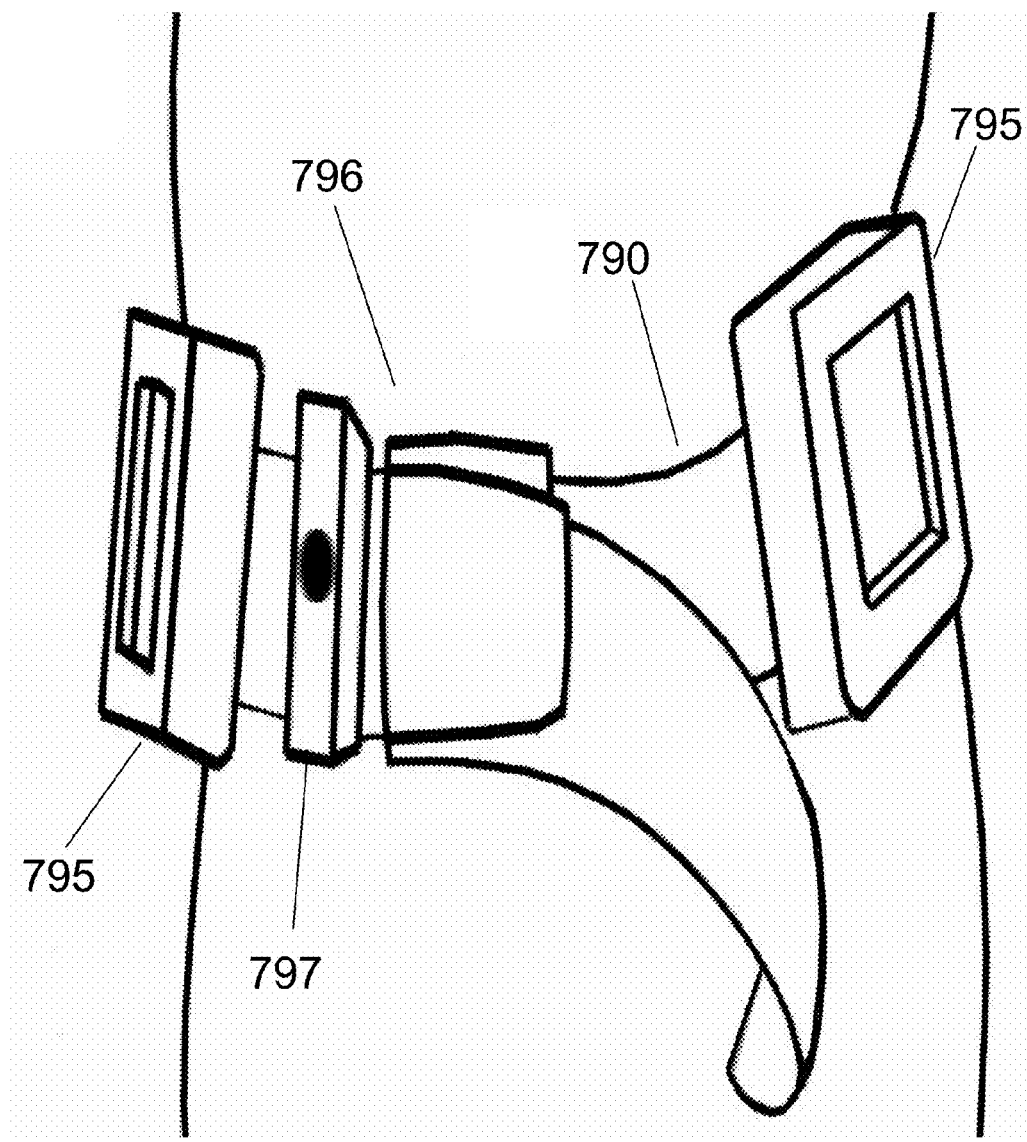
FIGS. 7A & B are schematic representations of a ballast belt as it may be used in the present invention.
Figure 7B:
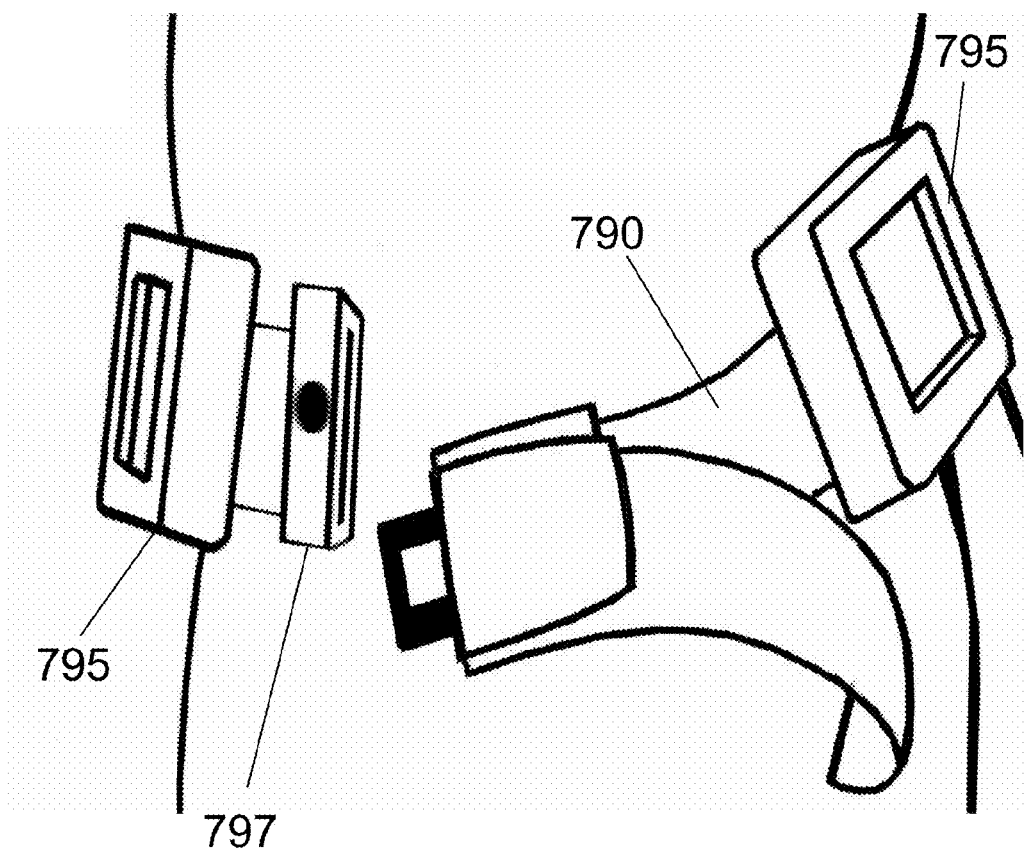

Attention is now turned to FIG. 7A which shows a diving belt 790 with weights 795 and a closable belt buckle 797 that is responsive to a controller element (not shown) of the present invention. The belt 790 may include a standard belt buckle 796 as well. Under normal diving conditions, the belt includes weights 795 in accordance with the diving depth desired and the buckle 797 is closed. FIG. 7B shows the responsive buckle 797 open in response to an emergency situation determined by an associated diver rescue element (not shown). By releasing the diving belt 790, a diver rescue element can allow for expedited return of the distressed diver to the surface. It is understood that individual weights 795 could be released rather than the entire diving belt 790.

Figure 8A:
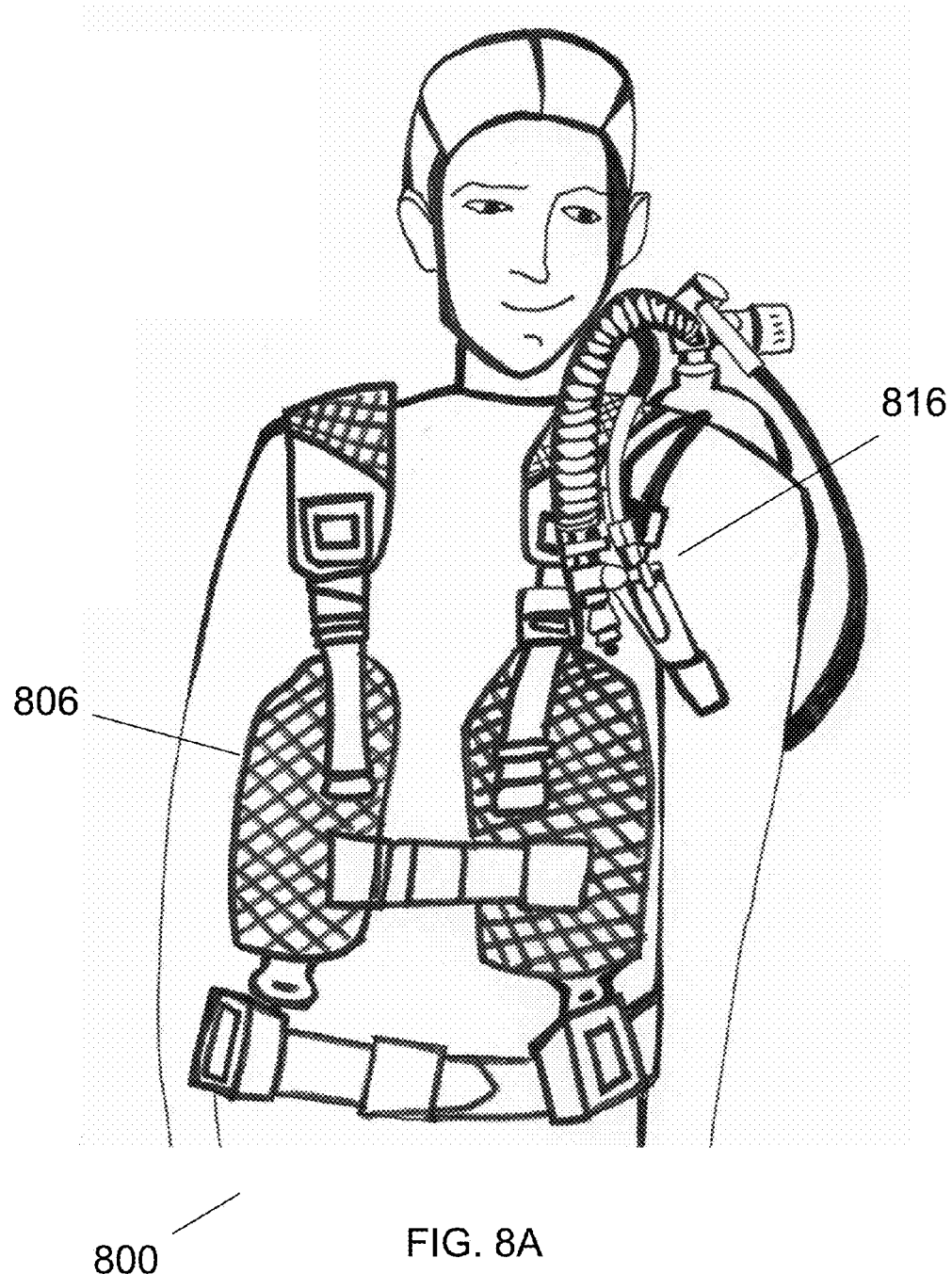
FIGS. 8A & B are schematic representations of an inflation vest as it may be used in the present invention.
Figure 8B:
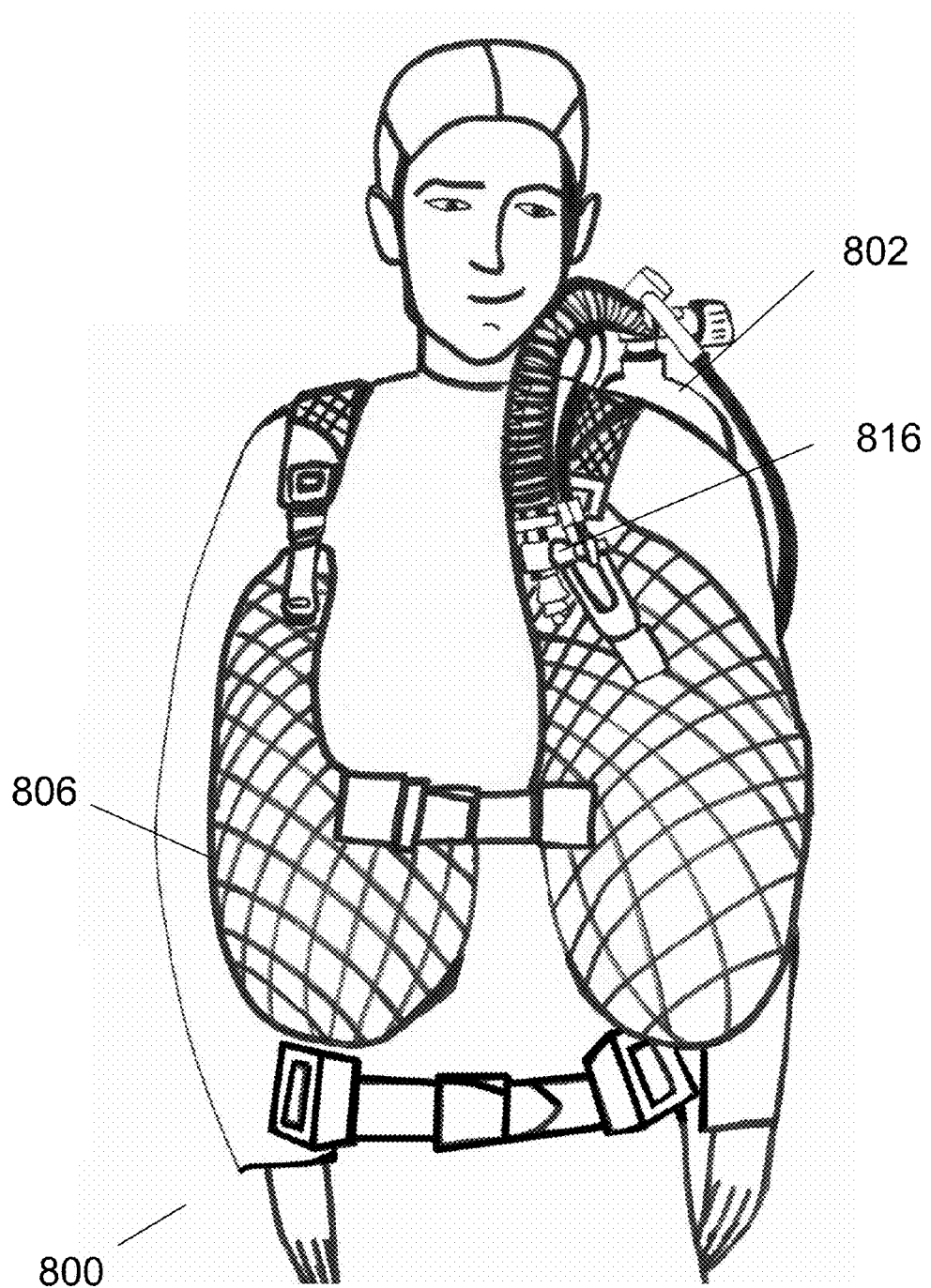

Attention is now turned to FIG. 8A which shows a diver 800 with an inflatable diving vest 806 associated with an inflator 816. In the figure, the diving vest 806 is deflated as it would be when diver 800. FIG. 8B shows the diving vest 806 inflated via inflator 816 from air tank 802. The present invention allows for diver-independent inflation of a diving vest 806 in response to a) gas pressure changes as measured by a diver rescue element (not visible in this view) and b) failure of the diver 800 to reset or turn off the diver rescue element— thus implying that the diver 800 is somehow incapacitated and in need of getting to the surface as quickly and safely as possible. Prior art inventions do not measure and respond in a fully automatic, diver-independent manner. Additionally, the present invention may be calibrated for breathing habits of a given diver 800 so as to respond according to his/her breathing behavior.

Sixth Embodiment

Attention is now turned to FIG. 9 which shows a method of the invention. The present invention includes a method for rescuing a distressed diver, including: providing a sensor for measuring air pressure in the diver's breathing system, wherein the sensor is in electric communication with an electronic controller; measuring air pressure patterns of the diver over periods of time with the controller; determining a change in the air pressure pattern is present wherein the change exceeds a predetermined value; and, activating a response element in response to the change in the air pressure pattern. The predetermined value for air pressure may be determined generally for specifically for a given diver. As such, the electronic controller may include elements for allowing it to communicate to a computer or other device, including but not limited to a USB connection or a WiFi chip. It is understood that at the time that a response element functions, air or oxygen is continued to be delivered to the diver himself/ herself.

Seventh Embodiment

Figure 10:
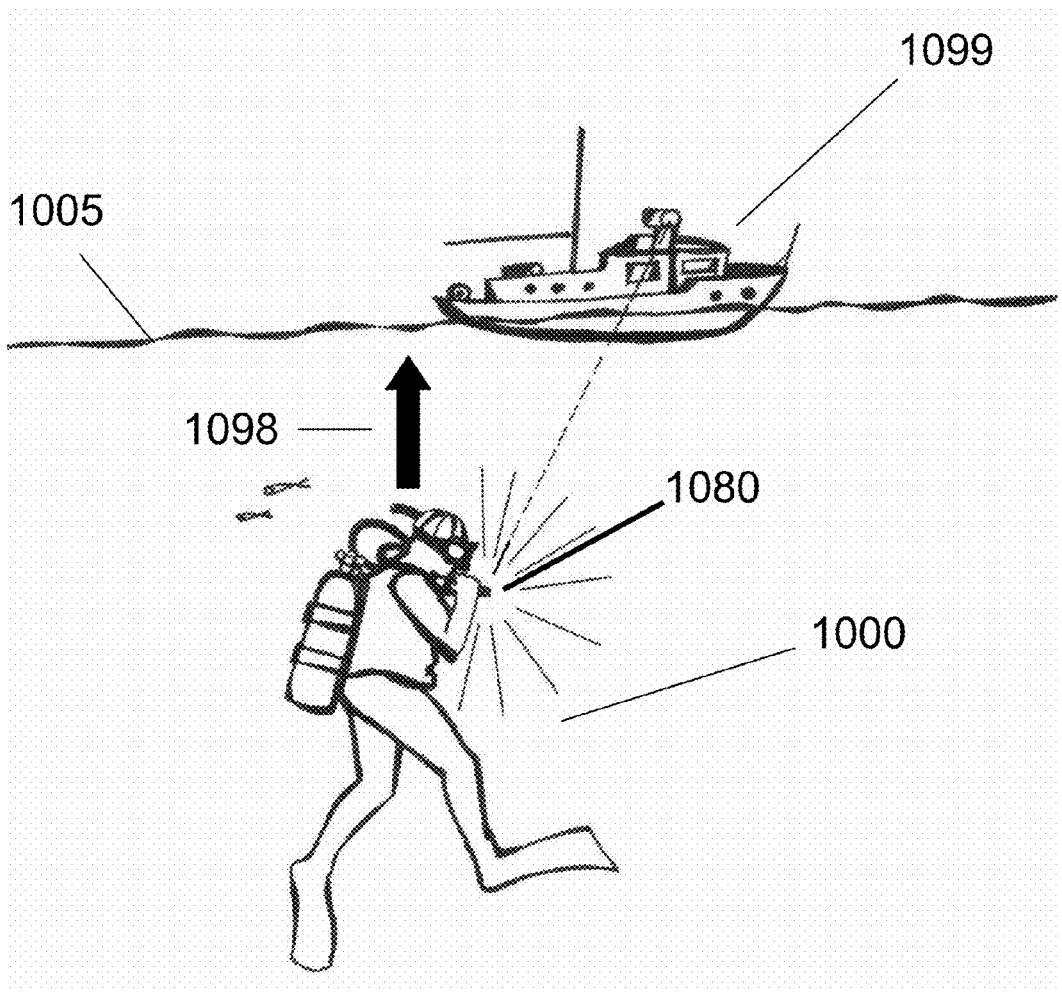
FIG. 10 is a schematic representation of an embodiment of the present invention as related to diver rescue.

Attention is turned to FIG. 10 which shows a diver 1000 heading towards 1098 the surface of a body of water 1005. The diver 1000 was underwater but was brought to the surface by action of his/her diver rescue element 1080. Below the surface and at the water surface, the diver rescue element 1080 alerts other divers (not shown) or crew on a nearby boat (1099) or land that the distressed diver 1000 needs attention. The diver rescue element 1080 may include transponders, cellular components, communication chips, and/or other elements that allow for alerting others as to the diver's position both underwater and on the surface of the water 1005.

Figure 11:
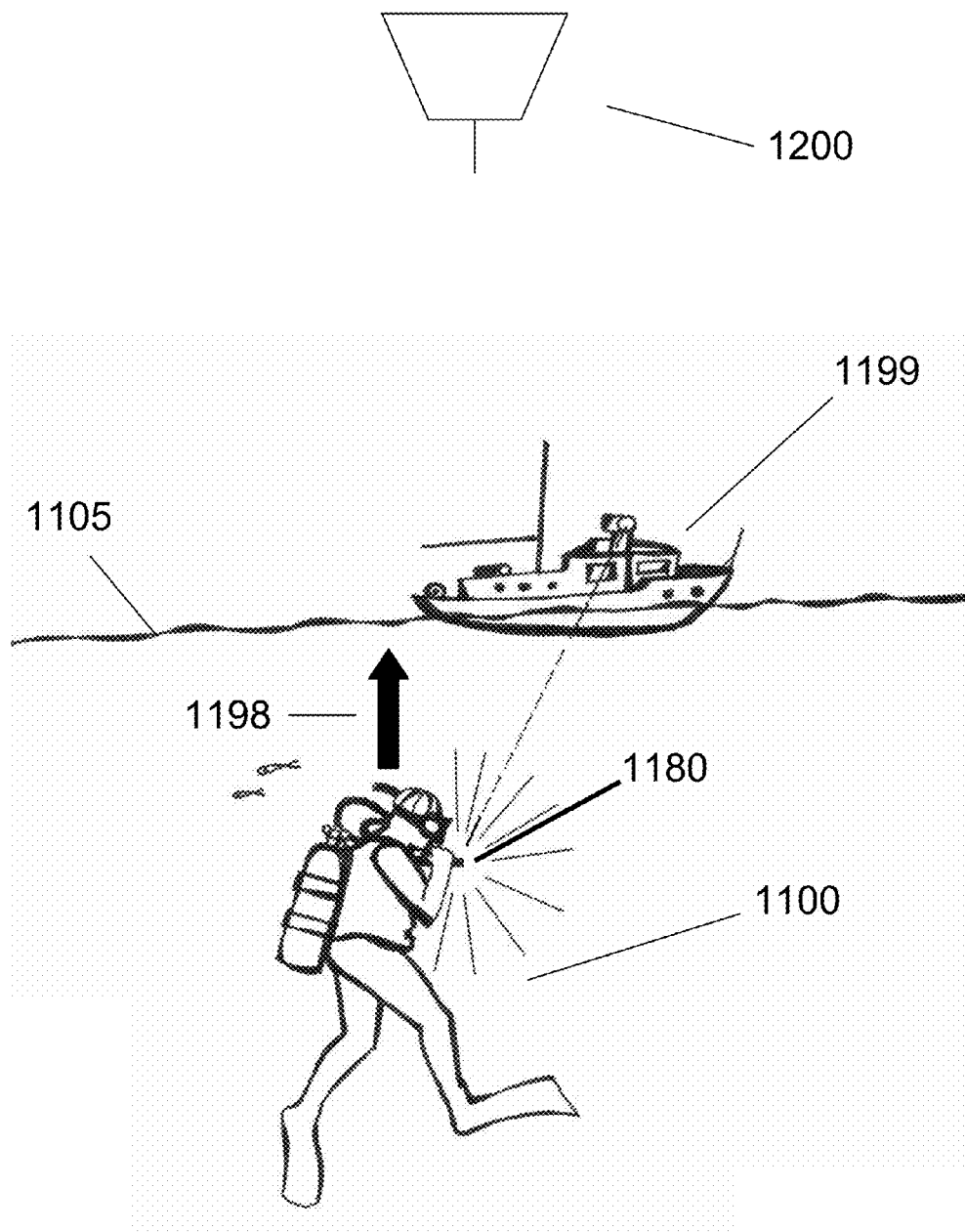
FIG. 11 is a schematic representation of an alternative embodiment of the present invention as related to diver rescue; and, FIG. 12 is a schematic drawing of a prototype of the present invention as described in the Examples.

Attention is now turned to FIG. 11 which shows a diver 1100 whose diver rescue element 1180 is in communication with at least one GPS satellite 1200 to allow for a nearby boat 1199 to head in the known direction of the distressed diver 1100 upon his/her heading 1198 towards the surface of a body of water 1105. The diver's diver rescue element 1180 includes both a GPS receiver as well as communication elements for sending GPS coordinates and possibly other data to others (these elements now shown separately in the figure) such as those on the boat 1199.

It is expected that during the life of a patent maturing from this application many relevant gas pressure detectors or breathing detectors will be developed and the scope of the term of the invention is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. The present invention could be employed with land-based breathing systems such as those used routinely by fire-fighters in order to save them should there be a cessation of breathing.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following example.

EXAMPLES

Reference is now made to the following example, which together with the above descriptions illustrates some embodiments of the invention in a non-limiting fashion.

Figure 12:
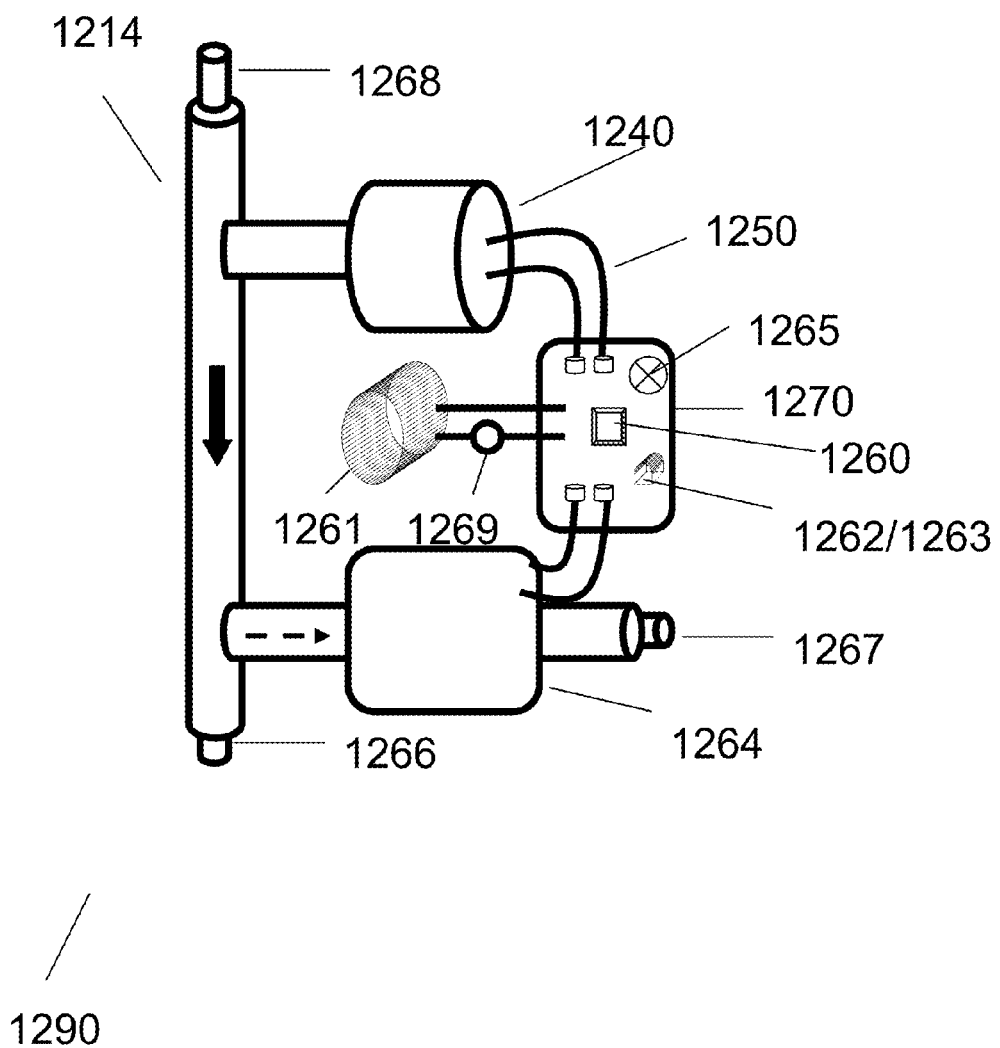

A prototype 1290 of the present invention was successfully constructed as herewith described and as shown schematically in FIG. 12. An air tube 1214 capable of connection to a diving tank (not shown) was attached to an air pressure sensor 1240 (Elcon PRM 26.6). The air pressure sensor 1240 was in electrical communication 1250 with a controller element 1260 (16F676-E) located on printed circuit board (PCB) 1270 that is powered by four 1.5 V double A batteries. The PCB 1270 is connected to the battery power source 1261, an LED light 1262, a buzzer 1263 (mcw1275) all of which are connected to the controller element 1260 through the PCB 1270. The controller element 1260 is additionally electrically contacted to a valve 1264 (Asco Joucomatic 18900002 solenoid valve) that controls air flow in response to instructions from the controller element 1260. Air that flows through the air tube 1214 enters from a tank at point 1268 and leaves for diver use at outlet 1266. In the event that controller element 1260 activated an emergency response, some of the air was directed by the valve 1264 towards an exit 1267 leading to an inflator hose (not shown). The prototype was tested and when no air pressure was detected or no change in air pressure was detected for 15 seconds, the LED light 1262 and the buzzer 1263 were activated. If during a 3 second period a reset button 1265 was not activated, air from the air tube 1214 was partially directed by the valve 1264 towards the exit 1267 leading to an inflator hose. Air was still directed towards the diver outlet 1266 during the partial diversion by valve 1264. This particular prototype included an on/off power switch 1269 independent of the reset button 1265, which restarts the 15 second counting period. The prototype will be placed in a waterproof container and used in sea trials.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for rescuing a distressed diver, including:
   providing a sensor for measuring air pressure in said diver's breathing system, wherein said sensor is in electric communication with an electronic controller;
   measuring air pressure patterns of said diver over periods of time with said controller;
   determining a change in said air pressure pattern is present wherein said change exceeds a predetermined value;
   alerting said diver to said change in said air pressure by means of an alarm;
   allowing said diver to prevent or stop a predetermined response and,
   activating a response element in the event that said diver does not activate a reset button during a predetermined period of time, wherein said response element includes a buoyancy component.

2. The method according to claim 1, further including the step of preprogramming said controller as to a medium pressure according to breathing patterns of said diver.

3. The method according to claim 1, wherein said predetermined response is selected from the following: sound alarm, alert others, inflate vest, release weights, alter buoyancy, release tank, and vibrate diver.

4. The method according to claim 1, wherein said response element includes any of the following features: lights, sounds, voice, and vibration.

5. The method according to claim 1, further including the step of modifying a diving depth of said diver.

6. The method according to claim 1, wherein said periods of time are predetermined.

7. A method for rescuing a distressed diver, including
   providing a sensor for air measuring air pressure in said diver's breathing system, wherein said sensor is in electronic communication with an electronic controller device and is associated with a diving inflator;
   determining with said sensor that said diver has a changed breathing pattern;
   activating an alarm; and,
   changing the buoyancy of said diver, when said diver does not activate a reset button associated with said alarm within a predetermined period of time, and allowing said diver, if conscious, to either continue surfacing or to manually deflate said diving inflator.

8. The method according to claim 7, wherein said alarm may be turned off by said diver.

9. The method according to claim 7, wherein said changing of the buoyancy is accomplished automatically through diverting some of said diver's air via a valve to said diver's inflator.

10. The method according to claim 2, further including programming said controller to recognize any anomalies recorded with respect to gas pressure or diver breathing.

11. The method according to claim 7, further including programming said controller to recognize any anomalies recorded with respect to gas pressure or diver breathing.

12. The method according to claim 11, wherein one manifestation of said anomalies is said diver not breathing.

13. The method according to claim 1, further including the step of programming said controller to communicate with a computer.

14. A method for rescuing a distressed diver, including:
providing a diving inflator, wherein said inflator is adapted to include a sensor for measuring air pressure in said diver's breathing system, wherein said sensor is in electric communication with an electronic controller;
measuring air pressure patterns of said diver over periods of time with said controller;
determining a change in said air pressure pattern is present wherein said change exceeds a predetermined value;
alerting said diver to said change in said air pressure by means of an alarm;
activating a response element in response to said change in said air pressure pattern in the event that said diver does not activate a reset button during said predetermined period of time, wherein said response element includes a buoyancy component; and
allowing said diver, if conscious, to either continue surfacing or deflate said buoyancy component.

15. The method according to claim 14, wherein said air pressure is medium air pressure.

16. The method according to claim 1, wherein said air pressure is medium pressure.

* * * * *